United States Patent [19]

Drozd et al.

[11] Patent Number: 4,560,657

[45] Date of Patent: Dec. 24, 1985

[54] MICROBIOLOGICAL PRODUCTION OF ALKYLENE OXIDES

[75] Inventors: Jan W. Drozd, Sittingbourne; Maureen L. Bailey, Ditton, Nr. Maidstone, both of United Kingdom

[73] Assignee: Shell Oil Company, Houston, Tex.

[21] Appl. No.: 515,711

[22] Filed: Jul. 20, 1983

[30] Foreign Application Priority Data

Jul. 21, 1982 [GB] United Kingdom ............ 8221113

[51] Int. Cl.$^4$ .................. C12P 17/02; C12N 1/20; C12R 1/32
[52] U.S. Cl. .................................. 435/123; 435/253; 435/863
[58] Field of Search ............... 435/123, 124, 249, 250

[56] References Cited

U.S. PATENT DOCUMENTS 4,347,319 5/1982 Hou et al. .................... 435/123
4,368,267 1/1983 Hou et al. .................... 435/123

FOREIGN PATENT DOCUMENTS 2018822 10/1979 United Kingdom .

OTHER PUBLICATIONS

DeBont, J. A. M. et al, *FEMS Microbiology Letters*, 6, (1979), pp. 183–188.
*Chem. Week Blad.*, Jun. 11, 1981, p. 215.

*Primary Examiner*—Lionel M. Shapiro
*Assistant Examiner*—Rebecca L. Thompson

[57] ABSTRACT

A process for the production of an alkylene oxide containing at least 3 carbon atoms which comprises cultivating an ethylene-utilizing microorganism under aerobic conditions in a liquid nutrient medium containing the corresponding alkene together with assimilable sources of nitrogen and essential mineral salts, the cultivation being carried out in the presence of ethylene in a molar proportion to alkene below 1:40.

10 Claims, No Drawings

MICROBIOLOGICAL PRODUCTION OF ALKYLENE OXIDES

This invention relates to the microbial oxidation of alkenes by means of ethylene-utilizing bacteria, especially of the *Mycobacterium* species.

It is known that ethylene and propylene can be oxidized to their respective oxides by the action of a variety of microbial species, and much of the work on such epoxidation has been carried out using micro-organisms which utilize $C_1$ compounds as a source of carbon and energy, e.g. methane-utilizing bacteria such and Methylosinus, Methylococcus and Methylobacterium. However, the alkylene oxide product often inhibits the growth and metabolism of the micro-organisms. It has been found that micro-organisms which can metabolize ethylene are markedly less susceptible to such inhibition, and hence the present invention is based on the application of such ethylene-utilizing bacteria to the oxidation of higher alkenes to the corresponding epoxide. This oxidation normally requires a co-factor (e.g. $NADH_2$) which is also oxidised and which has to be regenerated in its reduced form to permit continued reaction. This can, of course, be achieved by adding the co-factor as such, but a much more economically attractive alternative has been found in which it is generated microbially in situ by the co-oxidation of ethylene.

Accordingly, the present invention provides a process for the production of an alkylene oxide containing at least 3 carbon atoms which comprises cultivating an ethylene-utilizing micro-organism under aerobic conditions in a liquid nutrient medium containing the corresponding alkene together with assimilable sources of nitrogen and essential mineral salts, characterized in that the cultivation is carried out in the presence of ethylene in a molar proportion to alkene below 1:40.

The function of the ethylene, as explained above, is to provide a substrate for in situ microbial regeneration of the cofactor. However, if the molar proportion of ethylene to substrate alkene is too great the ethylene competes as substrate with the alkene and thereby causes a reduction in the desired product. Accordingly, as indicated above, the molar proportion of ethylene to substrate alkene should be below 1:40, and is preferably less than 1:100.

The process of the invention may, in principle, be carried out using any micro-organism which will oxidize ethylene, for example those belonging to the genera Nocardia, Brevibacterium, Corynebacterium and Mycobacterium, the choice normally being influenced by the nature of the substrate alkene and the consequential selection of an organism having an acceptable activity in the epoxidation of the chosen alkene. Likewise the process is applicable to many alkenes having 3 or more carbon atoms, which may be straight or branched chain and have terminal or internal double bonds, including those having more than one double bond such as butadiene and allene. A preferred embodiment of the process is the conversion of propylene to propylene oxide or 1-octene to 1,2-epoxyoctane, and Mycobacterium is the preferred organism for use in this embodiment, in particular the novel strain thereof isolated by the Applicants and deposited at the National Collections of Industrial Bacteria, Aberdeen Scotland under the accession number NCIB 11626.

The aerobic conditions required for the cultivation of the micro-organism can be provided according to any of the well-established procedures, provided that the supply of oxygen is sufficient not only to meet the metabolic requirements of the micro-organism but also to oxidize the alkene to its epoxide. This is most conveniently achieved by feeding a supply of gaseous oxygen, suitably as air, into the liquid nutrient medium along with the alkene.

The nutrient medium is normally aqueous, since this provides the most acceptable environment for the micro-organism, although the low solubility in water of the gaseous reactants makes it difficult to achieve a high reaction rate. One possible compromise is to operate with an aqueous/water immiscible organic two phase system in whose organic phase the alkene reactant is very soluble, and such a reaction medium is included within the term "liquid nutrient medium". The assimilable nitrogen in the nutrient medium is conveniently an ammonium salt, suitably in a concentration between 0.5 and 6.0 g nitrogen per liter. The temperature of cultivation and the time required to generate an acceptable yield of alkylene oxide naturally vary according to the alkene substrate and the micro-organism. In the case of propylene oxidation by Mycobacterium NCIB 11626 the temperature is suitably between 25° C. and 32° C. preferably 30° C., and for a batch process the cultivation time is normally between 10 and 100 hours. The micro-organisms may be present as a suspension in the nutrient medium or they may be immobilized onto a suitable support material according to established techniques. Alternatively, a cell-free extract may be used.

The rate of flow of substrate alkene, and the proportion of alkene:ethylene:air, are selected so as to optimize the production of the desired alkylene oxide. The optimal values will, of course, vary between different reaction systems, but their identification for any specific system is a matter of routine experimentation. In the case of propylene oxidation by Mycobacterium NCIB 11626, suitable ranges are 0.5 to 2 vols ethylene: 2 to 8 vols propylene: 4 to 12 vols oxygen, the preferred operating range being 1 vol ethylene: 4 vols propylene: 7 vols oxygen. The oxygen may be provided either as such, or as air, in which case the volumes will be 5 times greater.

As discussed above, the novel micro-organism Mycobacterium NCIB 11626 is very suitable for use in the application of the process of the invention to the oxidation or propylene to propylene oxide. This, and similar organisms, were isolated by inoculating soil samples from Kent into 250 ml shake flasks which each contained 100 ml of ASM medium and a gas atmosphere of air and ethylene, 1:1 v/v. The composition of ASM is as follows (in mM):

| | |
|---|---|
| $NH_4Cl$ | 10 |
| $KH_2PO_4$ | 3.9 |
| $Na_2HPO_4$ | 6.1 |
| $K_2SO_4$ | 1.0 |
| $MgSO_4$ | 0.15 |
| $CaCl_2$ | 0.05 |
| $FeSO_4$ | 0.020 |

The flasks were incubated at 30° C. on a rotary shaker with frequent changes of the gas atmosphere. After two to three weeks growth was visible and samples of the culture were plated onto ASM plates and incubated in a dessicator at 30° C. under a gas mixture containing equal volumes of air and ethylene. Cultures were purified by plating out in the usual manner. Purified cultures were stored on ASM agar slopes at 4° C., freeze-dried, and stored in liquid nitrogen. One of the cultures (designated T960) was identified by the staff of the National Collection of Industrial Bacteria at the Torry Research Station, Aberdeen, Scotland as a novel strain of Mycobacterium. This strain (NCIB 11626) has the following bacteriological characteristics. (determined according to the procedures and criteria described in Bergey's "Manual of Determinative Bacteriology", 8th Edition (1974) and Covan & Steel's "Manual for the Identification of Medical Bacteria").

set out below)+5 vols. deionised water, and the nutrients were fed into the fermenter vessel at the following rates:-Air 600 ml/hr; ethylene 70 ml/hr; Ammonium Hydroxide (2.2N) 5.6 ml/hr; defined salts 11.1 ml/hr, and deionised water 57.6 ml/hr, thereby providing a dilution rate of approx 0.02 hr$^{-1}$. The defined salt medium CSM B4 comprised:

| | |
|---|---|
| $H_3PO_4$ (2 M solution) | 60 ml/l |
| $K_2SO_4$ | 13.9 g/l |
| $MgSO_4.7H_2O$ | 9.87 g/l |

First Stage
Morphological descriptions are from growth on Oxoid CM3 Nutrient Agar except as stated

| | |
|---|---|
| Isolate | T.960 |
| °C. incubation | 30 |
| Cell morphology | Cells are irregular rods up to 2.5 $\mu M$ long. In stationary phase cultures the cells are shorter. Typical mycobacterium/corynebacterium shape. |
| Gram | Variable, or cannot stain. |
| Spores | — |
| Motility | Non-motile. |
| Flagella FM | |
| Colonial morphology | off-white low convex entire smooth translucent mucoid circular ½–1 mm in 2–3 days |
| °C., growth | 41°+ |
| | 45°− |
| Catalase | + |
| Oxidase, Kovacs | − |
| C—F glucose | − |
| First stage identification | Coryneform |

Second Stage

| Isolate | T960 | | T960 | | T960 |
|---|---|---|---|---|---|
| °C. incubation | 30 | | 30 | | 30 |
| Pyocyanin | | Gas glucose | — | Cell wall | meso-DAP |
| Fluorescence | | Acid glucose | — | diamino acid | not tested |
| DL-Arg CSU | | ONPG | | sugar | |
| Betaine CSU | | ARG Moller | | | |
| | | Lys Moller | | | |
| Glucose CSU | — | Orn Moller | | Fatty acid | Could be of |
| Lactate CSU | — | $NO_3$ to $NO_2$ | — | profile | Mycobacterium |
| Acetate CSU | | $NO_3$ to $N_2$ | — | | or |
| Sensitivity | | DNA ase | | | Rhodococcus |
| Penicillin G | | Gel stab 20° | — | Mycolic acids | Typical of |
| Streptomycin | | Gel plate | — | | Mycobacterium |
| Chloramphen | | Casein | — | | |
| Tetracycline | | Starch | — | | |
| Novobiocin | | Lecith egg | — | Acid fast | +(30° 4 days) |
| Polymyxin B | | Lipase egg | — | (Goodfellow & | |
| 0/129 | | $NH_3$ | | Alderson, 1977 | (strong or |
| Levan | | Indole | | Gordon, 1967) | partial not |
| | | | | (strong and | determined) |
| | | | | partial not | |
| | | | | defined) | |
| P HB accum | | MR | | | |
| Growth factor | | VP | | | |
| requirement | | 10% NaCl | — | | |
| | | Urease | — | | |

When high biomass concentrations of Mycobacterium NCIB 11626 are required, these have been obtained by an ammonia-limited continuous culture at 30° C. and pH 7.5. This culture was carried out in 4.4 liters of medium (see below), stirred at 950 rpm. To initiate growth ammonium chloride was added to give 2–5 mM final concentrations and 2-4N ammonium hydroxide used for pH control and nitrogen source until the desired biomass concentration (suitably 15 g/l) was attained. Thereafter, pH control was provided by 2–4M mixed sodium/potassium hydroxide. The medium comprised 1 vol. defined salts coded CSMB4 (composition

| | | |
|---|---|---|
| $CaCl_2.2H_2O$ | 1.47 g/l | |
| Trace Elements Medium | 20 ml/l | (Detailed |
| $FeSO_4.7H_2O$ (1 M solution) | 4 ml/l | below) |
| $CuSO_4.5H_2O$ (1 M solution) | 0.2 ml/l | |
| Trace Elements Medium contains: | | |
| (in g/l): | | |
| $ZnSO_4.7H_2O$ | 2.88 | |
| $MnSO_4.4H_2O$ | 2.23 | |
| $H_3BO_3$ | 0.62 | |
| $CuSO_4.5H_2O$ | 1.25 | |
| $Na_2MoO_4.2H_2O$ | 0.48 | |
| $CoCl_2.6H_2O$ | 0.48 | |

-continued

| | |
|---|---|
| KI | 0.83 |
| $H_2SO_4$ (IM solution) | 5 ml/l |

EXAMPLE

(A) Growth of cells from culture

Mycobacterium NCIB 11626 was continuously cultured at 30° C. and pH 6.6 in AM2 medium (see below), using ethylene as sole carbon and energy source at flow rates of 25 ml/min for ethylene and 400 ml/min for air. The medium was stirred at 500 rpm and fresh medium fed in at a dilution rate of 0.035 hr$^{-1}$. The composition of the AM2 medium was as follows:

| | | |
|---|---|---|
| $(NH_4)SO_4$ | 1.45 g/l | |
| $H_3PO_4$ (90%) | 1.09 g/l | |
| $MgSO_4.7H_2O$ | 0.099 g/l | |
| $CaCl_2.2H_2O$ | 0.015 g/l | |
| Trace Elements | 2 ml/l | (Detailed Below) |

Trace Elements TK3 contains (in g/l):

| | |
|---|---|
| $ZnSO_4.7H_2O$ | 1.44 g |
| $MnSO_4.4H_2O$ | 1.12 g |
| $H_3BO_3$ | 0.309 g |
| $CuSO_4.5H_2O$ | 0.624 g |
| $Na_2MoO_4.2H_2O$ | 0.242 g |
| $CoCl_2.6H_2O$ | 0.238 g |
| KI | 0.415 g |
| $H_2SO_4$ (IM) | 5.0 ml/l |

Cells were harvested from the fermenter by centrifugation at 20,000 g, washing once in 0.1M phosphate buffer and resuspended in the same.

(B) Epoxidation Reaction

Production of 1,2-epoxyoctane was carried out in 250 ml. flasks closed with a suba-seal. A two-phase system was used comprising 100 mg dry weight cells (obtained as in A above) in 5 ml of phosphate buffer as the aqueous phase and 10 ml of 55 octene in iso-octane as the organic phase.

A selected volume of ethylene gas was introduced into the flasks via the suba-seals using a syringe. 100 μl of the organic phase of each flask was sampled at intervals over 160 hrs, and analysed by G.L.C. These analyses for 1-octene and 1,2-epoxyoctane were carried out on a 5% JXR on Gas Chrom Q (100–200 mesh) glass column, 6 ft×2 mm, using a Varian Series 3700 gas chromatograph with flame ionization detection. The carrier gas flow was 30 ml $N_2$ with column temperature 80° C., and 1-octanol was used as the internal standard. The results of these experiments are set out in the Table below, from which it is clearly apparent that the presence of ethylene results in an increased yield of product provided that its concentrations is not so great as to compete with the 1-octene.

TABLE 1

| Ethylene added | | 1-octene added | Ratio | μmole product (1,2 epoxyoctane)* |
|---|---|---|---|---|
| Vol (ml) | μmol | μmol | $C_2H_4:C_8H_{16}$ | per hr per g dry wt cells |
| 0 | 0 | 3,180 | 0 | 50 |
| 0.2 | 8.92 | 3,180 | 1:356.5 | 127 |
| 2.0 | 89.2 | 3,180 | 1:35.65 | 81 |
| 5.0 | 223 | 3,180 | 1:14.3 | 51.3 |

*Rates integrated over 30 hrs.

We claim:

1. A process for the production of an alkylene oxide containing at least 3 carbon atoms which comprises cultivating an ethylene-utilizing microorganism Mycobacterium NCIB 11626 under aerobic conditions in the presence of ethylene and in a liquid nutrient medium containing the corresponding alkene together with assimilable sources of nitrogen and essential mineral salts.

2. Process as claimed in claim 1 wherein the alkene is propylene or 1-octene.

3. Process as claimed in claim 3 wherein the cultivation is carried out between 25° and 32° C.

4. Process according to claim 3 wherein the cultivation is carried out in an aqueous/water immiscible organic two phase system.

5. Process according to claim 3 wherein the microorganism is immobilized onto a suitable support material.

6. A process according to claim 2 wherein the alkene is octene.

7. A process according to claim 6 wherein the ratio of ethylene to octene is less than 1:40.

8. A process according to claim 2 wherein the alkene is propylene.

9. Process as claimed in claim 8 wherein the cultivation is carried out continuously using flow rates in the range 0.5–2 vols ethylene: 2–8 vols alkene: 4–12 vols oxygen.

10. A biologically pure culture of Mycobacterium NCIB 11626.

* * * * *